United States Patent [19]

Payne

[11] Patent Number: 5,324,517
[45] Date of Patent: Jun. 28, 1994

[54] SPRAYABLE ADHESIVE FOR GYPSY MOTH PHEROMONE BEADS

[75] Inventor: Charles C. Payne, Aurora, Ill.

[73] Assignee: Nalco Chemical Company, Naperville, Ill.

[21] Appl. No.: 37,315

[22] Filed: Mar. 26, 1993

Related U.S. Application Data

[63] Continuation of Ser. No. 866,200, Apr. 9, 1992, abandoned.

[51] Int. Cl.$^5$ ............................................. A01N 25/24
[52] U.S. Cl. .................................... 424/407; 424/405; 424/408; 424/84
[58] Field of Search ............... 424/405, 84, 407, 408, 424/487

[56] References Cited

U.S. PATENT DOCUMENTS 4,291,052  9/1981  Gillings et al. ..................... 424/382
4,983,390  1/1991  Levy ................................... 424/404
5,061,697  10/1991  Shasha et al. ........................ 514/60

OTHER PUBLICATIONS

Beroza, Ed. ACS Symposium Series 23, 1976, pp. 104, 105 Pest Management with Insect Attractants.

Primary Examiner—Thurman K. Page
Assistant Examiner—Neil Levy
Attorney, Agent, or Firm—Robert A. Miller; Joan I. Norek; James J. Drake

[57] ABSTRACT

An adhesive composition for a insect-control agent, such as gypsy moth pheromone beads, provides retention and water insolubility to such pesticide upon deposit of an aqueous mixture of such adhesive composition and insect-control agent. The adhesive composition concentrate comprises a salt such as sodium sulfate, an ethoxylated alkylphenol, a polymeric adhesive material, and a high molecular weight acrylate polymer.

5 Claims, No Drawings 5,324,517

SPRAYABLE ADHESIVE FOR GYPSY MOTH PHEROMONE BEADS

This is a continuation of application Ser. No. 07/866,200, filed Apr. 09, 1992, now abandoned.

TECHNICAL FIELD OF THE INVENTION

The present invention is in the technical field of compositions containing insect-control agents, mainly pheromone beads that can be applied to foliage by spraying the composition, particularly when the spraying is conducted from an airplane.

BACKGROUND OF THE INVENTION

The North American strain of gypsy moths (species *Lymantria dispar*), or its ancestral European strain, has been known in North America since the later 1800's, and by 1889 serious damage from this strain of gypsy moth was being-reported in wooded areas by researchers. Gypsy moths are considered devastating insect pests in their larva stage when they are leaf-eating caterpillars. These caterpillars can ravage entire forests. As adults, the gypsy moths do not have working mouth parts, so they cannot feed, and they live only a few days or weeks. The North American gypsy moths have wings, but cannot use them to fly. Instead they catch a breeze and glide on it. Thus the spread of this strain of gypsy moth is not considered rapid, and researchers are able to wipe out centers of infestation when detected. Thus to an extent the North American strain of gypsy moth has been suppressed, but since it is found in forests in New England, the Northeast, and the Mid-Atlantic states, and has also been detected as far west as the Pacific Northwest, over the many decades of efforts it clearly has not been eradicated.

In the early 1980's the Asian strain of gypsy moth was introduced to North America, apparently being transported aboard foreign trade vessels that docked in Seattle, in Portland, Oreg., and in Vancouver, British Columbia. The caterpillars of this strain have been observed using tiny threads of silk to become airborne, permitting them to be carried off like kites, and thus the caterpillars themselves spread to acres of forests inland. The capability of this Asian strain to spread is believed intensified by the fact that the females have working wings. The females fly. Their spread is more rapid than the North American strain and hence wiping out a center of infestation is a much more difficult task. It is possible that the Asian strain has spread throughout most of the North American continent.

The Asian strain of gypsy moth is also more threatening than the North American strain because of the caterpillars' eating habits. They are more voracious eaters and they feast on more varieties of trees than the North American gypsy moth caterpillars. While preferring oak, they will feed on almost any tree or shrub. Known hosts include alder, apple, basswood, birch, box elder, hawthorn, hazelnut, mountain ash, poplar, willow and witch hazel trees, rose bushes, and sumac plants.

The introduction of the Asian strain of gypsy moth is believed to be adding to the destruction of thousands of trees and is leading to the increased use of insect-control agents. The watersheds in Washington, Oregon and British Columbia are in jeopardy of damage. The national forests of the United States are believed in jeopardy. North American agriculture may be threatened, and is already burdened with the costs of suppressing these strains of gypsy moths.

The term "insect-control agent" is defined as any chemical that can alter or destroy the normal life cycle of the insect in question. Chemicals which can fall into this category are insecticides, miticides, phermones, and the like.

One weapon being used to combat the gypsy moth problem is displarlure, a sex pheromone, which is known to disrupt the procreation cycle of at least the North American strain of gypsy moth. The pheromone has been used to lure the males to insecticides or to physical traps. Such traps, however, provide too limited an area of protection when the plant life to be protected extends over vast areas, which at times can be millions of acres.

For large scale protection, one currently used method is to incorporate such pheromone as beads into a composition that can be sprayed over acres of foliage and there become attached to leaves and tree limbs and stems and the like, so that a male gypsy moth, now being attracted to the surrounding multiple sources of the pheromone, becomes distracted to the point of procreation failure. The males cannot located females in such environment.

Such large scale protection requires the pheromone beads to be well distributed throughout the canopy of a forest or other foliage area to be protected. Such distribution is best achieved by spraying a pheromone bead-containing composition from above, and therefore from an airplane. The pheromone bead-containing composition must have a viscosity that is sufficiently low for spraying. The pheromone bead-containing composition must include an adhesive or sticker (discussed in more detail below) which adheres the pheromone beads to the foliage that comes into contact with the composition. The pheromone bead-containing composition, as sprayed, generally contains a high level of water, and thus the various components of such composition are typically diluted with water prior to spraying to achieve a sprayable mixture. Such dilution, when the composition is sprayed from an airplane, is routinely made in-flight, using a simple recirculating pump to admix the various components prior to spraying.

An adhesive or sticker formulation, to be suitable for use for large scale spraying from an airplane, thus must be readily dispersible with water, so as to be thoroughly admixed with the water and the pheromone beads using a simple recirculating pump. The adhesive or sticker therefore must not only have the desired adhesive properties, which are discussed in more detail below, but also have the relatively low viscosity required for rapid water dispersibility using only simple admixing means such as a recirculating pump.

To be suitable for spraying from an airplane, the pheromone bead-containing composition must predictably fall to the target area, and not drift with the wind. Thus the droplets formed upon spraying must be of sufficient size. To provide suitably sized droplets generally drift control agents are used. Drift control agents are compositions that promote coalescence of fine droplets into larger droplets or strands of droplets, for instance fine mists of from about 200 to about 800 microliters or strands of several inches long, which size range is generally considered suitable to minimize the drifting of compositions when sprayed. A drift control agent for use in pheromone bead-containing compositions, however, must also be readily water dispersible, and must not interfere with the performance of the adhesive or sticker. A typical drift control agent will interfere with the performance of a sticker and will be difficult to disperse in water using a simple recirculating pump or the like without the inclusion of a water miscible solvent of some type in the drift control formulation. Such type of solvents, however, generally will add flash point characteristics to the formulation which is not desirable.

As to the adhesive or sticker performance, as discussed more filly below, the adhesive should provide not merely good bonding between the pheromone beads and the foliage, but also bonding that is resistant to weather conditions, particularly rain and wind.

It is an object of the present invention to provide an adhesive formulation that can be used with pheromone beads, dusts, flakes, powder and the like solid forms of this distracter, and other pesticides for which there are similar use techniques and performance goals. It is an object of the present invention to provide such adhesive formulation that provides excellent water insolubility characteristics to the deposit film. It is an object of the present invention to provide such an adhesive formulation that provides excellent retention of the active components, such as the pheromone beads, on the foliage. It is an object of the present invention to provide such an adhesive formulation that is readily dispersible in water without any high energy admixing and thus can be readily admixed with simple equipment such as a recirculating pump. It is an object of the present invention to provide such an adhesive formulation that provides a pheromone bead-containing composition, or the like, that can be easily sprayed from an airplane, not only because of its water dispersibility, but also because of its drift properties. It is an object of the present invention to provide such an adhesive formulation without the use of any flash point creating solvents. It is also an object of the present invention to provide pheromone bead-containing compositions including such an adhesive formulation, and a method for using such pheromone bead-containing formulation. These and other objections of the present invention are described in more detail below.

DISCLOSURE OF THE INVENTION

The present invention provides an adhesive composition for an insect-control agent, which adhesive composition provides retention and water insolubility to the insect-control agent upon its deposit in an aqueous mixture onto foliage. Such adhesive composition is comprised of:

- from about 0.01 to about 5.0 parts by weight of an inorganic salt, such as sodium sulfate;
- from 0 to about 0.03 parts by weight of an ethoxylated alkylphenol;
- from about 1 to about 60 parts by weight of a polymeric adhesive solids;
- from about 0.015 to about 1.5 parts by weight of an high molecular weight acrylate polymer solids as the salt form;
- and water.

The present invention also provides a method for preparing such an adhesive composition, a sprayable mixture including such an adhesive composition, an insect-control agent and dilution water. The present invention also provides a method for distributing such an insect-control agent by spraying. These and other embodiments of the invention are described more fully below.

PREFERRED EMBODIMENTS OF THE INVENTION

The sprayable adhesive of the present invention may be considered a fortified or combination adhesive. It may be used as, or as a substitute for, stickers that are employed to increase the retention of sprays or dust deposits on plants by resisting the various factors involved in weather. Stickers used commercially may include proteinaceous materials, such as milk products, wheat flour, blood albumin and gelatin, oils, gums, resins and fine clays. Some commercially used stickers produce elastic films when deposited on leaves. Many stickers also possess some wetting and spreading characteristics, such as stickers that consist of the salts of sulfates or sulfated alcohols, esters of fatty acids, alkyl sulfonates and petroleum sulfonates. Generally, a sticker is a substance which increases the firmness of attachment of finely-divided solids or other water-soluble materials to a surface. A sticker's performance of may be measured in terms of its resistance to time, wind, water, mechanical, and at times chemical, action.

Heretofore most commercially available stickers suffer from poor water insolubility, low retention properties, and/or ease of application, particularly when the most desired application method is spraying. These "deficiencies" of commercial stickers generally either arise from attempts to employ such stickers for a demanding application, such as the spray distribution of pheromone beads, or become more apparent when tried for such a use. In contrast, the present invention provides a fortified adhesive that:

(1) Can be used with pheromone beads, dusts, flakes, powders and the like solid forms of pheromone, and other insect-control agents for which there are similar use techniques and performance goals;
(2) Provides excellent water insolubility to the deposit film;
(3) Provides excellent retention of the pheromone beads and the like on the host foliage;
(4) Is readily dispersible in water and thus is easily diluted with water; and
(5) Can be sprayed from an airplane without drift problems.

The purpose of distributing pheromone beads is to provide a confusion source, and for that purpose persistency of the bonding between the beads and host foliage is highly desired. The pheromone beads are not consumed in their intended performance. The distribution of pheromone beads is not an application where, after placement, a slow release of the active component is desired. Thus certain characteristics of some commercial stickers, such as slow degradation of the deposit film, render such stickers unsuitable for other than temporary persistency of the pheromone beads, while instead the greatest degree of persistency is desired. The very optimum desired performance of a sticker for pheromone beads is to provide a bond to the foliage for as long as a pheromone bead continues to act as a sex lure to the male gypsy moth, or as long as such host foliage survives. A slow release of the pheromone beads over a time period of a few weeks or so is a deposit characteristic that counters the optimization of the use of pheromone beads.

A good performance of the adhesive properties of a pheromone bead-containing composition, upon deposit on foliage surfaces, particularly on leaf surfaces, requires preferably a retention of at least about 50 or 60 percent of the pheromone beads at a low pheromone beads to adhesive ratio, despite adverse weather conditions, such as rain and high winds, and greater retention performance, for instance the retentions of 80 or 90 percent or more of the pheromone beads, is highly desirable. A good performance of the adhesive properties of a pheromone bead-containing composition, upon deposit on foliage surfaces, particularly on leaf surfaces, requires preferably that the adhesive, as deposited, provides water insolubility to the pheromone beads despite severe rain conditions, for instance continuous rain in mounts of 4 or 5 inches of rain. A good performance of the adhesive properties of a pheromone bead-containing composition, upon deposit on foliage surfaces, particularly on leaf surfaces, requires preferably that the water insolubility properties of the deposits develop within only a short time period, and survive for long time periods. A commercial scale distribution of the pheromone beads should not be thwarted by rainfalls that occur a couple of hours later, nor should the deposits unduly lose the desired water insolubility and find resistance during dry periods, regardless of whether such periods continue for weeks. Moreover, the persistence desired of the deposits makes it preferable that the desired retention and water insolubility properties, which provide the desired resistance to rain and wind, continue without undue diminishment, for at least 3 or 4 weeks, and preferably even longer time periods, after the initial distribution. The combination adhesive of the present invention meets such performance standards, and at times surpasses them, at low concentrations of the formulation in the spray mixture, and hence low pheromone beads to adhesive ratios.

Wide scale distribution of pheromone beads to the canopy of a forest or other foliage area in need of protection from gypsy moth infestation is required. Such wide scale distribution often necessitates the spraying of the composition from an airplane, using only simple equipment, such as a recirculating pump and the like, for admixing the adhesive with the dilution water and the pheromone beads, as discussed above. Any formulation that is to be so diluted in-flight should have a viscosity of no more than about 2,000 cps Brookfield, and preferably it should have viscosities that are lower than this ceiling. The various embodiments of the adhesive formulation of the present invention routinely have viscosities within the range of from about 100 to about 1000 cps Brookfield, and thus are well under the practical viscosity ceiling. The various embodiments of the adhesive formulation of the present invention have been found to be readily dispersible in water without the incorporation of any solvent that may provide flash point characteristics to the formulation.

The adhesive formulation of the present invention further incorporates a high molecular weight polymer of the type that is used in drift control agents, without any loss of the low-viscosity characteristics, and is believed to alone provide sufficient drift control without the incorporation into the spray mixture of any additional additives.

The advantageous use of the adhesive formulation of the present invention as the sole component to be admixed with the dilution water and pheromone beads simplifies the formation of the diluted spray mixture, and is a preferred embodiment of the present invention.

In an embodiment, the present invention is an adhesive composition for a insect-control agent, which adhesive composition provides retention and water insolubility to the insect-control agent upon its deposit in an aqueous mixture onto foliage. Such adhesive composition is comprised of:

from about 0.01 to about 5.0 parts by weight of an inorganic salt such as sodium sulfate;

from 0 to about 0.03 parts by weight of an ethoxylated alkylphenol;

from about 1 to about 60 parts by weight of a polymeric adhesive solids;

from about 0.015 to about 1.5 parts by weight of an high molecular weight acrylate polymer solids as the salt form;

and water. The ethoxylated alkylphenol is a $C_{6-10}$ alkyl phenoxy ethoxyethanol, wherein the alkyl may be linear or branched chained, and wherein the ethoxyethanol substituent has about 6 or more ethoxy units, and has an HLB of at least 10. The polymeric adhesive is a polyacrylate multipolymer mixture or a polyurethane dispersion. The high molecular weight acrylate polymer has an intrinsic viscosity of at least about 18, a mole percent of acrylic acid mer units of from about 5 to about 50, and a mole percent of acrylamide mer units of from about 50 to about 95, the acrylic polymer being in the salt form. The amount of the water is sufficient to provide the composition with a viscosity of no more than 2,000 cps Brookfield. Such adhesive composition would also contain any oil or surfactants or the like that are incorporated together with any of the components as supplied, before the components are admixed to form this adhesive composition. Such other materials are not believed to be in any way active components of the adhesive composition, and therefore, while their presence is not believed deleterious to the composition, such inadvertent materials are not enumerated above.

In preferred embodiments, as to this adhesive composition: the salt such as sodium sulfate is present in the composition in an amount from about 1.0 to about 2.25 parts by weight same basis; the ethoxylated alkylphenol is present in the composition in an amount from about 0.001 to about 0.02 parts by weight same basis; the polymeric adhesive is present in the composition in an amount from about 20 to about 50 parts by weight same basis; and/or the high molecular weight acrylate polymer is present in the composition in an amount from about 0.45 to about 1.1 parts by weight same basis.

The adhesive composition in another preferred embodiment is a composition comprised of:

from about 0.01 to about 5.0 percent of the inorganic salt such as sodium sulfate;

from 0 to about 0.03 percent of the ethoxylated alkylphenol;

from about 1 to about 60 percent of the polymeric adhesive solids;

from about 0.015 to about 1.5 percent of the high molecular weight acrylate polymer solids as the salt form;

and the balance the water.

In another preferred embodiment the adhesive composition is a composition comprised of:

from about 0.01 to about 5.0 percent of the inorganic salt such as sodium sulfate;

from 0 to about 0.03 percent of the ethoxylated alkylphenol;

from about 1 to about 60 percent of the polymeric adhesive solids;

from about 0.015 to about 1.5 percent of the high molecular weight acrylate polymer solids as the salt form;

and the balance the water.

In another preferred embodiment the adhesive composition contains as the polymeric adhesive is a polyacrylate multipolymer, described in more detail below.

In further preferred embodiment, the high molecular weight acrylate polymer is comprised of from about 20 to 40 mole percent of sodium acrylate mer units and from about 60 to about 80 mole percent of the acrylamide met units.

The present invention, in another embodiment, is a method of preparing an adhesive composition for a insect-control agent that provides retention and water insolubility to the insect-control agent upon deposit of an aqueous mixture of the adhesive composition and the insect-control agent on foliage, comprising admixing:

from about 0.01 to about 5.0 parts by weight of an inorganic salt such as sodium sulfate;

from 0 to about 0.03 parts by weight of an ethoxylated alkylphenol;

from about 15 to about 75 parts by weight of an adhesive;

from about 0.5 to about 5 parts by weight of an acrylic polymer latex;

and water;

wherein the ethoxylated alkylphenol is a $C_{6-10}$ alkyl phenoxy ethoxyethanol, wherein the alkyl may be linear or branched chained, and wherein the ethoxyethanol substituent has about 6 or more ethoxy units;

wherein the adhesive is a polyacrylate multipolymer mixture or a polyurethane dispersion containing from about 30 to about 65 weight percent polymer solids;

wherein the acrylic polymer latex is a water-in-oil emulsion containing from about 20 to about 40 weight percent of an acrylic polymer as polymer solids, the acrylic polymer having an intrinsic viscosity of at least about 18, a mole percent of acrylic acid mer units of from about 5 to about 50, and a mole percent of acrylamide mer units of from about 50 to about 95, the acrylic polymer being in the salt form; and wherein the amount of the water admixed is sufficient to provide the composition with a viscosity of no more than 2,000 cps Brookfield.

In a preferred embodiment, the method above more particularly comprises admixing:

from about 1.0 to about 2.25 parts by weight of the salt such as sodium sulfate;

from 0.001 to about 0.02 parts by weight of the ethoxylated alkylphenol;

from about 20 to about 50 parts by weight of the adhesive;

from about 1.5 to about 3.5 parts by weight of the acrylic polymer latex;

and 55 to 75 parts by weight water;

wherein the admixing results in an adhesive composition containing a total of about 100 parts by weight.

In another embodiment, the present invention provides a sprayable aqueous mixture for distributing a insect-control agent that provides retention and water insolubility to the insect-control agent upon deposit of an aqueous mixture of the adhesive composition and the insect-control agent on foliage, comprising:

from about 0.01 to about 5.0 parts by weight of an inorganic salt such as sodium sulfate;

from 0 to about 0.03 parts by weight of an ethoxylated alkylphenol;

from about 1 to about 60 parts by weight of a polymeric adhesive solids;

from about 0.015 to about 1.5 parts by weight of an high molecular weight acrylate polymer solids as the salt form;

from about 20 to about 50 parts by weight of the insect-control agent; and from about 40 to about 80 parts by weight water;

wherein the ethoxylated alkylphenol is a $C_{6-10}$ alkyl phenoxy ethoxyethanol, wherein the alkyl may be linear or branched chained, and wherein the ethoxyethanol substituent has about 6 or more ethoxy units;

wherein the polymeric adhesive is a polyacrylate multipolymer mixture or a polyurethane dispersion;

wherein the high molecular weight acrylate polymer has an intrinsic viscosity of at least about 18, a mole percent of acrylic acid mer units of from about 5 to about 50, and a mole percent of acrylamide mer units of from about 50 to about 95, the acrylic polymer being in the salt form; and wherein the amount of the water is sufficient to provide the mixture with a viscosity of no more than 2,000 cps Brookfield.

In preferred embodiments, the above described mixture contains pheromone beads as the insect-control agent and has a viscosity of no more than 1,000 cps Brookfield.

The present invention in another embodiment is a method of distributing an insect-control agent comprising spraying a mixture a described above onto foliage. In preferred embodiment the spraying is conducted in-flight from an airplane. In another preferred embodiment the insect-control agent that is sprayed is pheromone beads.

The Test Procedure

The following laboratory test procedure measures the retention of. deposits of pheromone beads from droplets on plant foliage and the resistance of such deposits to various weather conditions, namely rain, strong wind, and variations in time elapse between application and rain or heavy wind conditions. The retention by resistance to rain aspect of the test is also a determination of the water insolubility of the deposits. In all instances the pheromone beads used arc commercially available pheromone beads under the tradenames Agri 129 bead or Raccmio Disparlure bead, both from AgriSense Company of Fresno, Calif. Formulations containing an adhesive are prepared and diluted with water and admixed with the pheromone beads to provide the test mixtures (defined in more detail below under "Standard Mixture"). The concentration of pheromone beads in the Standard Mixture is commensurate to that of mixtures as sprayed in commercial applications. One droplet of a given mixture is hand placed onto each of five leaves (northern red oak foliage). One droplet is approximately 500 microliters and contains about 20 pheromone beads. The leaves arc then left lying at ambient room temperature and humidity for a predetermined drying period, after which they are exposed a water spray and/or mechanical agitation simulating respectively rainfall (in controlled and measured amount and rate) and wind (in standard degree and time duration). The number of pheromone beads on each leaf is counted after the drying period and again after exposure to simulated rain and/or wind, with the assistance of a standard dissecting microscope. The retention of the pheromone beads is reported as "Percent Recovery", that is:

$$\frac{\text{Number of beads on a leaf after weather treatment}}{\text{Number of beads on a leaf before weather treatment}} \times 100 = \text{Percent Recovery}$$

Unless otherwise stated, the Percent Recovery reported herein for a given test is the average of the five replicates (five leaves). A Percent Recovery that is greater than 100 percent is typically the result of small beads being hidden from view when initially counted, which are exposed by the weather treatment.

As seen from the description above, the Test Procedure is a simulated laboratory procedure wherein retention and water insolubility is measured. As noted elsewhere herein, it is desirable that a sprayable mixture for pheromone beads and the like also have drift control performance. Such drift control performance can generally, however, be determined without actually spraying a diluted mixture, and the mixtures prepared for the Examples below are believed to have a sufficient degree of drift control, and hence require no other additives for this purpose.

The Standard Mixture

The Standard Mixture for the various Examples, the Control and the Comparative Examples below is as follows:

| | |
|---|---|
| 37 parts by weight | pheromone beads |
| 63-(a + b + c) parts by weight | soft water |
| a parts by weight | commercial drift control agent, when used |
| b parts by weight | a commercial sticker, when used |
| c parts by weight | the Combination Adhesive |
| 100 parts by weight | concentrate for the Standard Mixture | which concentrate is then diluted as needed with water to provide a Standard Mixture containing about 20 pheromone beads per 500 microliters.

The Commercial Drift Control Agent

In all instances, there is no commercial drift control agent except that used in the Control described below. That commercial drift control product is comprised of a high molecular weight polymer having visco-elastic properties, held in the water phase of a water-in-oil latex, surfactants, a sulfonate and a water miscible organic solvent, and has a Brookfield viscosity before product dilution of about 1800 cps.

The Commercial Sticker

Two different commercial stickers were used in either the "Control" formulation or in the Comparative Examples. These commercial stickers are designated herein as S-1 and S-2, and can be described generally as adhesive types of materials known for use in pheromone bead application formulations. The S-1 sticker is a carboxylated styrene butadiene resin type of adhesive.

The Control

The Control in all instances it is used in the following Examples is a combination of the S-1 commercial sticker and the drift control agent. In terms of the Standard Mixture formulation given above, the Control contains 20 parts by volume of the commercial drift control product, which contains about 1 percent actives, and the concentration "b" of commercial sticker in the Control's Standard Formulation ("b") is 3 parts by weight per hundred parts by weight of sprayable mixture.

The Combination Adhesive

The Combination Adhesive is a formulation within the present invention, and its composition, as conveniently supplied for dilution with water, and of course addition of the pheromone beads, is as follows:

| Component | General Weight Percentage | Preferred Weight Percentage |
|---|---|---|
| Soft Water | balance | 55 to 75% |
| Sodium sulfate | 0.01 to 5.0% | 1.0 to 2.25% |
| Ethoxylated alkylphenol | 0 to 0.03% | 0.001 to 0.02% |
| Adhesive Emulsion | 15 to 75% | 20 to 50% |
| Acrylate Polymer Emulsion | 0.5 to 5% | 1.5 to 3.5% |

Unless indicated otherwise, the Combination Adhesive as used in the following Examples is as shown above wherein all weight percentages of all the components are with the "preferred weight percentage" ranges. It is used alone, without any commercial sticker or commercial drift control product. The Adhesive Emulsion is preferably comprised of a polyacrylate multipolymer mixture or a polyurethane composition, or mixtures thereof, supplied in latex form. Such latices have a solids content of from about 1 to about 60, for the purpose of employing the general and preferred percentages therefor given above. The Acrylate Polymer Emulsion is a water-in-oil ("w/o" or oil external) emulsion more fully described below. The ethoxylated alkyl phenol is a $C_{6-10}$ alkyl phenoxy ethoxyethanol, wherein the alkyl may have a linear or branched chain and the ethoxyethanol substituent may contain about 6 or more ethoxy units ($—CH_2CH_2O—$), and preferably have an HLB of 10 or above. Such ethoxylated alkyl phenols are well known nonionic surfactants commercially available under the tradenames of Triton X, Igepal, Polytergent and others.

The Acrylate Polymer Emulsion

The Acrylate Polymer Emulsion, as set forth for the Combination Adhesive described above, more specifically is comprised of a high molecular weight polymer having an Intrinsic Viscosity ("IV") of greater than about 18 or 20, and the polymer actives comprise from about 28 to 32 weight percent of this Emulsion. The polymer is comprised of from about 15 to about 35 mole percent sodium acrylate met units and from about 65 to about 85 mole percent acrylamide met units.

The Combination Adhesives used in the following Examples have viscosities, prior to dilution and addition of the pheromone beads of from about 100 to about 700 cps Brookfield, and thus such Combination Adhesives are easily dispersed in the dilution water.

The high molecular weight acrylate polymer is of the same type as used in the above described commercial drift control product, but again the combination, or fortified, adhesive composition of the present invention does not contain any flash point creating solvent.

The various Combination Adhesive formulations used in the following Examples are designated C-1, C-2, C-3, C-4, and C-5. Of these, C-1 and C-5 contain a polyurethane type of adhesive, and the others contain a multipolymer polyacrylate type of adhesive.

Typical polyurethane dispersions are those available under the tradename of Bayhydrol, from Miles, Inc. These polyurethane dispersions have from about 35 to about 40 weight percent solids and exhibit a viscosity of less than about 1000 cps. One such product which has been found particularly useful is Bayhydrol 121.

Typical polyacrylate multipolymers are mixtures of (meth)acrylate esters of $C_{6-10}$ alcoh including an hydroxy-substituted ester such as 2-hydroxyethyl acrylate, butyl acrylate, and methyl methacrylate, to provide a somewhat flexible, but nontacky, adhesive, together with a polymer promoting water insolubility, such as a styrene-methacrylic acid copolymer. Typical polyacrylate multipolymers are commercially available under the UCAR tradename from Union Carbide. These products contain from about 40 to about 60 weight percent polymer solids and have viscosities of less than about 100 cps. One such product preferred for use in the present invention is the UCAR-100 latex.

EXAMPLES 1 to 8

Standard mixtures were prepared containing from 3 to 13 weight percent of combination adhesives C-1 and C-2 described above. The Test Procedure described above was employed to determine the Percent Recovery performances of such standard mixtures in resisting the equivalent of 5 inches of rain after a two-hour drying period, and also after a 24-hour drying period for the higher concentration standard mixtures. The test results, including identification of the standard mixture concentration, the duration of the drying period, and the respective combination adhesive used are set forth below in Table 1, together with the performance test results for the Control under the same set of parameters.

TABLE 1

Five Inches Rain Weather Condition

| Example No. | Combination Adhesive | Concentration "c" (weight percent) | Drying Period (hours) | Percent Recovery |
|---|---|---|---|---|
| 1 | C-1 | 3 | 2 | 116% |
| 2 | C-1 | 6 | 2 | 125% |
| 3 | C-1 | 13 | 2 | 102% |
| 4 | C-1 | 13 | 24 | 113% |
| 5 | C-2 | 3 | 2 | 46% |
| 6 | C-2 | 6 | 2 | 100% |
| 7 | C-2 | 13 | 2 | 104% |
| 8 | C-2 | 13 | 24 | 95% |
| Control | none | — | 2 | 4% |
| Control | none | — | 2 | 11% |
| Control | none | — | 2 | 29% |
| Control | none | — | 24 | 28% |

EXAMPLES 9 to 12 and COMPARATIVE EXAMPLES A and B

Standard mixtures were prepared containing either 13 or 25 weight percent of Combination Adhesives C-1, C-3, C4 and C-5 described above, and for comparison two standard mixtures were prepared using commercial stickers. In Comparative Example A the commercial sticker is S-1, known to be a carboxylated styrene butadiene resin. The composition of the S-2 commercial sticker used in Comparative Example B is not known. The Test Procedure described above was employed to determine the Percent Recovery performances of such standard mixtures in the resistance of the equivalent of 0.5 and 1.0 inches of rain after a two hour drying period. The test results, including identifications of the standard mixture concentrations and the combination adhesive or commercial sticker used, are set forth below in Table 2.

TABLE 2

Two Hour Drying Time Condition

| Example or Comparative Example No. | Combination Adhesive | Concentration "c" or "b" (weight percent) | Percent Recovery 0.5" Rain | 1.0" Rain |
|---|---|---|---|---|
| 9 | C-3 | 13% | 65% | 65% |
| 10 | C-4 | 25% | 88% | 66% |
| 11 | C-5 | 13% | 100% | 98% |
| 12 | C-1 | 25% | 112% | 130% |
| A | * | 13%* | 97% | 97% |
| B | ** | ** | 29% | 32% |

*13% of S-1 commercial sticker
**unknown concentration of S-2 commercial sticker

EXAMPLES 13 to 16 and COMPARATIVE EXAMPLES C and D

Standard mixtures were prepared containing either 13 or 25 weight percent of Combination Adhesives C-1, C-3, C-4 and C-5 described above, and for comparison two standard mixtures were prepared using commercial stickers. In Comparative Example C the commercial sticker was the same S-1 as used in Comparative Example A and is known to be a carboxylated styrene butadiene resin. The composition of the commercial sticker used in Comparative Example D was the same S-2 as used in Comparative Example B. The Test Procedure described above was employed to determine the Percent Recovery performance of such standard mixtures in the resistance of the equivalent of 0.5 and 1.0 inches of rain after a five hour drying period. The test results, including identifications of the standard mixture concentrations and the combination adhesive or commercial sticker used, are set forth below in Table 3.

TABLE 3

Five Hour Drying Time Condition

| Example or Comparative Example No. | Combination Adhesive | Concentration "c" or "b" (weight percent) | Percent Recovery 0.5" Rain | 1.0" Rain |
|---|---|---|---|---|
| 13 | C-3 | 13% | 131% | 115% |
| 14 | C-4 | 25% | 100% | 100% |
| 15 | C-5 | 13% | 80% | 70% |
| 16 | C-1 | 25% | 93% | 100% |
| C | * | 13%* | 108% | 114% |
| D | ** | ** | 114% | 121% |

*13% S-1 commercial sticker
**S-2 commercial sticker

EXAMPLES 17 and 18

Two standard mixtures were prepared using 13 weight percent of the Combination Adhesives designated C-1 and C-2 respectively, and the Test Procedure described above was used to determine the drying time period required for development of water insolubility and rain resistance. The drying time periods varied from 30 to 360 minutes and the rain condition employed was the severe 5 inches of rain simulation. The Control standard mixture, described above, was also put through the same series of tests. The test results versus the drying times are set forth below in Table 4. Example 17 uses C-1 adhesive; Example 18 uses C-2.

TABLE 4

Five Inches Rain Condition/13 Percent Combination Adhesive

| Example No. | Percent Recovery Drying Time Period | | | | | |
|---|---|---|---|---|---|---|
| | 30 Min. | 60 Min. | 90 Min. | 120 Min. | 240 Min. | 360 Min. |
| Control | 1 | 9 | 14 | 24 | 38 | 43 |
| 17 | 2 | 33 | 107 | 106 | 90 | 88 |
| 18 | 7 | 36 | 95 | 95 | 94 | 97 |

EXAMPLES 19 to 24

Six standard mixtures were prepared using from 3 to 10 weight percent of the Combination Adhesives designated C-1 and C-2 respectively, and the Test Procedure described above was used to determine, for a 2 hour drying time period, the water insolubility and rain resistance properties of these standard mixtures. The rain conditions employed varied from a mild 1 inch to the severe 5 inches of rain simulation. The Control standard mixture, described above, was also put through the same series of tests. The test results versus the inches of rain are set forth below in Table 5. Examples 19 to 21 use the C-1 adhesive; Examples 22 to 24 use the C-2 adhesive.

TABLE 5

Two Hour Drying Time Condition

| Example No. | Concentration "c" (percent by weight) | Percent Recovery Inches of Rain | | | |
|---|---|---|---|---|---|
| | | 1 Inch | 2 Inches | 3 Inches | 5 Inches |
| Control | — | 12 | 11 | 11 | 9 |
| 19 | 3% | 41 | 32 | 33 | 23 |
| 20 | 6% | 104 | 100 | 93 | 88 |
| 21 | 10% | 113 | 110 | 106 | 85 |
| 22 | 3% | 130 | 120 | 124 | 93 |
| 23 | 6% | 98 | 85 | 93 | 86 |
| 24 | 10% | 111 | 95 | 109 | 92 |

EXAMPLES 25 and 26

Two standard mixtures were prepared using 10 weight percent of the Combination Adhesives designated C-1 and C-2 respectively, and the Test Procedure described above was used to determine the drying time period required for development of water insolubility and rain resistance. The drying time periods varied from 30 to 360 minutes and the rain condition employed was the severe 5 inches of rain simulation, as was done in Examples 17 and 18 above. The Control standard mixture, described above, was also put through the same series of tests. The test results are set forth below in Table 6. Example 25 uses C-1 adhesive; Example 26 uses C-2.

TABLE 6

Five Inches Rain Condition/10 Percent Combination Adhesive

| Example No. | Percent Recovery Drying Time Period | | | | | |
|---|---|---|---|---|---|---|
| | 30 Min. | 60 Min. | 90 Min. | 120 Min. | 240 Min. | 360 Min. |
| Control | 2 | 15 | 9 | 29 | 63 | 87 |
| 25 | 0 | 5 | 39 | 74 | 61 | 41 |
| 26 | 3 | 2 | 82 | 33 | 102 | 102 |

EXAMPLES 27 8and 28

Two standard mixtures were prepared using 6 weight percent of the Combination Adhesives designated C-1 and C-2 respectively, and the Test Procedure described above was used to determine the drying time period required for development of water insolubility and rain resistance. The drying time periods varied from 30 to 120 minutes and the rain condition employed was the severe 5 inches of rain simulation, similar to the tests of Examples 17, 18, 26 and 27 above. The Control standard mixture, described above, was also put through the same series of tests. The test results are set forth below in Table 7. Example 27 uses the C-1 adhesive; Example 28 uses C-2.

TABLE 7

Five Inches Rain Condition/6 Percent Combination Adhesive

| Example No. | Percent Recovery Drying Time Period | | | |
|---|---|---|---|---|
| | 30 Min. | 60 Min. | 90 Min. | 120 Min. |
| Control | 0 | 26 | 9 | 7 |
| 27 | 47 | 36 | 82 | 102 |
| 28 | 15 | 58 | 53 | 56 |

EXAMPLES 29 to 34

Six standard mixtures were prepared using either 3 or 6 weight percent of the Combination Adhesives designated C-1, C-4 and C-2 respectively, and the Test Procedure described above was used to determine, for a 2 hour drying time period, the water insolubility and rain resistance properties to the severe rain condition of 5 inches of rain simulation. The Control standard mixture, described above, was also put through the 5 inches of rain test. The test results and the amount and type of adhesive used are set forth below in Table 8.

TABLE 8

Two Hour Drying Time Condition

| Example No. | Combination Additive | Concentration "c" (percent by weight) | Percent Recovery 5 Inches Rain |
|---|---|---|---|
| Control | — | * | 4 |
| 29 | C-1 | 3% | 116 |
| 30 | C-1 | 6% | 125 |
| 31 | C-4 | 3% | 15 |
| 32 | C-4 | 6% | 60 |
| 33 | C-2 | 3% | 46 |
| 34 | C-2 | 65 | 100 |

EXAMPLES 35 to 46

Twelve standard mixtures were prepared using from 10 to 26 weight percent of each of the Combination Adhesives designated C-1, C-5, C-4, and C-3, and the Test Procedure described above was used to determine both the rain resistance and wind resistance properties of the deposits of these mixtures after a drying period of 19 days. Separate groups of leaves were used for the rain resistance and the wind resistance tests. The identities of the Combination Adhesives, their concentrations, the amount of rain and the duration of the wind employed for the tests, and the test results, are set forth below in Table 9.

TABLE 9

| | | Drying Period of 19 Days | | |
|---|---|---|---|---|
| Example No. | Combination Adhesive | Concentration "c" (Weight Percent) | Percent Recovery 5 Inches Rain | Percent Recovery Two Hours Fan Wind |
| Control | — | — | 86 | 100 |
| 35 | C-1 | 26 | 95 | 101 |
| 36 | C-1 | 13 | 65 | 90 |
| 37 | C-1 | 10 | 102 | 103 |
| 38 | C-5 | 26 | 92 | 95 |
| 39 | C-5 | 13 | 93 | 72 |
| 40 | C-5 | 10 | 78 | 101 |
| 41 | C-4 | 26 | 89 | 99 |
| 42 | C-4 | 13 | 90 | 93 |
| 43 | C-4 | 10 | 81 | 76 |
| 44 | C-3 | 26 | 81 | 99 |
| 45 | C-3 | 13 | 67 | 98 |
| 46 | C-3 | 10 | 16 | 95 |

EXAMPLES 47 to 58

Twelve standard mixtures were prepared using from 10 to 26 weight percent of each of the Combination Adhesives designated C-1, C-5, C-4, and C-3, and the Test Procedure described above was used to determine both the rain resistance and wind resistance properties of the deposits of these mixtures after a drying period of 33 days. Separate groups of leaves were used for the rain resistance and the wind resistance tests. The identities of the Combination Adhesives, their concentrations, the amount of rain and the duration of the wind employed for the tests, and the test results, are set forth below in Table 10.

TABLE 10

| | | Drying Period of 19 Days | | |
|---|---|---|---|---|
| Example No. | Combination Adhesive | Concentration "c" (Weight Percent) | Percent Recovery 5 Inches Rain | Percent Recovery Two Hours Fan Wind |
| Control | — | — | 95 | 99 |
| 47 | C-1 | 26 | 99 | 101 |
| 48 | C-1 | 13 | 98 | 101 |
| 49 | C-1 | 10 | 100 | 101 |
| 50 | C-5 | 26 | 82 | 99 |
| 51 | C-5 | 13 | 69 | 97 |
| 52 | C-5 | 10 | 47 | 97 |
| 53 | C-4 | 26 | 91 | 94 |
| 54 | C-4 | 13 | 89 | 96 |
| 55 | C-4 | 10 | 90 | 86 |
| 56 | C-3 | 26 | 89 | 97 |
| 57 | C-3 | 13 | 58 | 100 |
| 58 | C-3 | 26 | 47 | 84 |

The inorganic salt is including in the various compositions for viscosity control, and of the many inorganic salts available, it is believed that sodium salts are preferred, and while a sodium salt such as sodium chloride could of course be employed, sodium sulfate provides more ions per mole and is preferred for such viscosity control purpose.

The term "foliage" as used herein includes, but is not limited to, leaves.

Unless otherwise expressly stated herein, all percentages are weight percentages.

Industrial Applicability of the Invention

The present invention is applicable to the forestry and agriculture industries and any other industries employing insect-control agents.

I claim:

1. A sprayable aqueous mixture for distributing a insect-control agent that provides retention and water insolubility to said insect-control agent upon deposit of an aqueous mixture of said adhesive composition and said insect-control agent on foliage, comprising:
   from about 0.01 to about 5.0 parts by weight of an inorganic salt;
   from 0 to about 0.03 parts by weight of an ethoxylated alkylphenol;
   from about 1 to about 60 parts by weight of a polymeric adhesive solids;
   from about 0,015 to about 1.5 parts by weight of an high molecular weight acrylate polymer solids as the salt from;
   from about 20 to about 50 parts by weight of said insect-control agent; and
   from about 40 to about 80 parts by weight water;
   wherein said ethoxylated alkylphenol is a $C_{6-10}$ alkyl phenoxy ethoxyethanol, wherein said alkyl may be linear or branched chained, and wherein said ethoxyethanol substituent has at least about 6 ethoxy units;
   wherein said polymeric adhesive is a polyacrylate multipolymer mixture or a polyurethane dispersion;
   wherein said high molecular weight acrylate polymer has an intrinsic viscosity of at least about 18, a mole percent of acrylic acid met units of from about 5 to about 50, and a mole percent of acrylamide met units of from about 50 to about 95, said acrylic polymer being in the salt form;
   wherein the amount of said water is sufficient to provide said mixture with a viscosity of no more than 2,000 cps Brookfield; and
   wherein said insect-control agent is pheromone beads.

2. A sprayable aqueous mixture for distributing a insect-control agent that provides retention and water insolubility to said insect-control agent upon deposit of an aqueous mixture of said adhesive composition and said adhesive composition and said insect-control agent on foliage, comprising:
   from about 0.01 to about 5.0 parts by weight of an inorganic salt;
   from 0 to about 0.03 parts by weight of an ethoxylated alkylphenol;
   from about 1 to about 60 parts by weight of a polymeric adhesive solids;
   from about 0.015 to about 1.5 parts by weight of an high molecular weight acrylate polymer solids as the salt from;
   from about 20 to about 50 parts by weight of said insect-control agent; and
   from about 40 to about 80 parts by weight water;
   wherein said ethoxylated alkylphenol is a $C_{6-10}$ alkyl phenoxy ethoxyethanol,
   wherein said alkyl may be linear or branched chained, and wherein said ethoxyethanol substituent has at least about 6 ethoxy units;
   wherein said polymeric adhesive is a polyacrylate multipolymer mixture or a polyurethane dispersion;
   wherein said high molecular weight acrylate polymer has an intrinsic viscosity of at least about 18, a mole percent of acrylic acid mer units of from about 5 to about 50, and a mole percent of acrylamide mer units of from about 50 to about 95, said acrylic polymer being in the salt form; and wherein the amount of said water is sufficient to provide said mixture with a viscosity of no more than 1,000 cps Brookfield.

3. A method of distributing a insect-control agent comprising:
spraying the mixture of claim 1 onto foliage.

4. The method of claim 3 wherein said spraying is conducted in-flight from an airplane.

5. The method of claim 3 wherein said insect-control agent is p

UNITED STATES PATENT AND TRADEMARK OFFICE
CERTIFICATE OF CORRECTION

PATENT NO. : 5,324,517
DATED : JUNE 28, 1994
INVENTOR(S) : CHARLES C. PAYNE

It is certified that error appears in the above-identified patent and that said Letters Patent is hereby corrected as shown below:

COLUMN 16, LINE 12, CLAIM 1 from about 0,015 to about 1.5 parts by weight of an

LETTERS PATENT SHOULD READ AS:

from about 0.015 to about 1.5 parts by weight of an

COLUMN 16, LINE 28 & 29, CLAIM 1 percent of acrylic acid met units of from about 5 to about 50, and a mole percent of acrylamide met

LETTERS PATENT SHOULD READ AS:

percent of acrylic acid mer units of from about 5 to about 50, and a mole percent of acrylamide mer Signed and Sealed this Sixth Day of September, 1994

Attest:

BRUCE LEHMAN

*Attesting Officer*  *Commissioner of Patents and Trademarks*